United States Patent
Baek

(10) Patent No.: US 11,504,266 B2
(45) Date of Patent: Nov. 22, 2022

(54) SNORING PREVENTION PILLOW

(71) Applicant: Youngjin Baek, Daegu (KR)

(72) Inventor: Youngjin Baek, Daegu (KR)

( * ) Notice: Subject to any disclaimer, the term of this patent is extended or adjusted under 35 U.S.C. 154(b) by 0 days.

(21) Appl. No.: 17/637,422

(22) PCT Filed: Sep. 23, 2020

(86) PCT No.: PCT/KR2020/012878
§ 371 (c)(1),
(2) Date: Feb. 22, 2022

(87) PCT Pub. No.: WO2021/101057
PCT Pub. Date: May 27, 2021

(65) Prior Publication Data
US 2022/0265464 A1  Aug. 25, 2022

(30) Foreign Application Priority Data

Nov. 20, 2019 (KR) .................. 10-2019-0149352

(51) Int. Cl.
*A47C 19/00* (2006.01)
*A47C 19/02* (2006.01)
*A61F 5/56* (2006.01)
*A47G 9/10* (2006.01)

(52) U.S. Cl.
CPC . *A61F 5/56* (2013.01); *A47G 9/10* (2013.01)

(58) Field of Classification Search
CPC .............. A47G 9/109; A47G 9/10; A61F 5/56
USPC ......................................................... 5/636
See application file for complete search history.

(56) References Cited

U.S. PATENT DOCUMENTS

| 4,748,702 A * | 6/1988 | Sandler ........... A61F 5/56 5/636 |
| 5,781,947 A * | 7/1998 | Sramek .......... A47G 9/109 5/636 |
| 5,848,448 A * | 12/1998 | Boyd ............. A47G 9/10 5/636 |
| 11,259,657 B1 * | 3/2022 | Molina ........... A47G 9/0253 |

(Continued)

FOREIGN PATENT DOCUMENTS

| KR | 10-2013-0034912 A | 4/2013 |
| KR | 10-1293259 B1 | 8/2013 |

(Continued)

OTHER PUBLICATIONS

International Search Report for PCT/KR2020/012878 dated Dec. 30, 2020 from Korean Intellectual Property Office.

*Primary Examiner* — Myles A Throop
(74) *Attorney, Agent, or Firm* — Revolution IP, PLLC

(57) ABSTRACT

A snoring prevention pillow includes: a center protrusion (101) allowing sleeper's head and neck to laterally rotate in either left or right direction at the center of upper and lower surfaces of a pillow body (10); a neck support (102) formed on lower portions of the upper and lower surfaces of the pillow body (10); and headrest portions (103) formed at opposite sides of the center protrusion (101) and each having a groove shape that is thinner than the pillow body (10), wherein the headrest portions (103) each have the groove that becomes deeper from the lower to upper portion in the upper lateral direction such that the head and the neck of the sleeper can be tilted in the upper lateral direction.

1 Claim, 4 Drawing Sheets

(56) References Cited

U.S. PATENT DOCUMENTS

| | | | | |
|---|---|---|---|---|
| 2012/0110742 A1* | 5/2012 | Lawler | ............... | A61G 13/121 |
| | | | | 5/636 |
| 2012/0179202 A1* | 7/2012 | Pham | ................. | A61H 1/0296 |
| | | | | 606/240 |
| 2015/0245967 A1* | 9/2015 | Horng | .................. | A61G 7/072 |
| | | | | 128/845 |
| 2017/0156958 A1* | 6/2017 | Roh | ..................... | A47G 9/109 |
| 2019/0069698 A1* | 3/2019 | Lin | ..................... | A47G 9/1009 |
| 2020/0085611 A1* | 3/2020 | Peters | ..................... | A61F 5/56 |
| 2020/0205590 A1 | 7/2020 | Kang | | |
| 2020/0214481 A1* | 7/2020 | Sexton | ............... | A61H 1/0218 |
| 2020/0375382 A1* | 12/2020 | Park | ................... | A47G 9/1081 |
| 2021/0235900 A1* | 8/2021 | Choi | ................. | A47G 9/1009 |

FOREIGN PATENT DOCUMENTS

| | | |
|---|---|---|
| KR | 20-0474341 Y1 | 9/2014 |
| KR | 10-1825882 B1 | 2/2018 |
| KR | 10-2018-0031098 A | 3/2018 |
| KR | 10-2018-0071218 A | 6/2018 |

\* cited by examiner

SNORING PREVENTION PILLOW

CROSS REFERENCE TO PRIOR APPLICATIONS

This application is a National Stage Application of PCT International Patent Application No. PCT/KR2020/012878 filed on Sep. 23, 2020, under 35 U.S.C. § 371, which claims priority to Korean Patent Application No. 10-2019-0149352 filed on Nov. 20, 2019, which are all hereby incorporated by reference in their entirety.

TECHNICAL FIELD

The present invention relates to a snoring prevention pillow, and more particularly, to a snoring prevention pillow configured to allow the head and neck of a sleeper to rotate in any one of left and right directions and to extend in an upper lateral direction at the same time when the sleeper lies back on the pillow to sleep so that curved postures of the cervical spine and atlanto-occipital joint are induced and supported so as to maintain smooth respiratory circulation during sleep and to prevent snoring, apnea, and opening of the mouth of the sleeper during sleep.

BACKGROUND ART

Snoring is respiratory noise caused by a respiratory air flow generating vibrations in peripheral structures such as a relaxed velum (a relatively soft rear part of a palate), the uvula (a shape drooping downward from a center of a velum of an oral cavity), and the like while passing through the respiratory tract narrowing due to a variety of causes.

That is, snoring occurs when the larynx through which air passes before entering the respiratory tract while people breathe narrows and thus air cannot easily pass therethrough. When people breathe, air passes through flexible structures such as the palate, uvula, tonsil, tongue, and the like. Here, since peripheral muscles relax and droop during sleep, the larynx partially narrows. When air passes through the larynx which has narrowed, vibrations occur in a gap between peripheral soft parts such that snoring occur.

Meanwhile, among very severe snoring patients, the larynx which is a path of air for respiration may be temporarily blocked due to serious muscle relaxation during sleep, serious obesity, or other causes. Here, air cannot be supplied to lungs, which is called sleep apnea syndrome.

Meanwhile, snoring is noise physically having a frequency characteristic of about 500 Hz and sometimes intensity thereof reaches 80 to 90 dB. This exceeds 40 to 60 dB which is a noise exposure level of a work place of general workers according to industrial safety and health standards. In consideration of defining that a worker should necessarily wear soundproof protector in a work place exposed to noise maintained more than 80 dB, it may be estimated how loud severe snoring is.

Accordingly, when a person is continuously exposed to the noise of severe snoring, the person may have an auditory disorder (noise-induced deafness). When snoring and apnea recur during sleep everyday, hypoxy is caused, which adversely affects the heart and vascular system, and thus high blood pressure, arteriosclerosis, arrhythmia, a heart attack, and the like are caused. In addition, deep sleep is prevented and thus the person feels drowsiness and tiredness in the daytime. Accordingly, the person often has a headache such that job performance is degraded and daytime sleepiness causes irritability, anxiety, depressive reactions, and the like.

As a method of curing snoring, largely, there are a surgical treatment method and a non-surgical treatment method.

The surgical treatment method varies according to a part causing snoring. There are surgeries such as a nasal cavity operation (correction with respect to septum deviation and hypertrophy of the inferior nasal concha), a pharyngeal operation (palatopharyngoplasty for cutting mucous membrane of the tonsils and oropharynx and high-frequency thermal palatectomy), tongue reduction surgery, head and neck surgery (genioglossus muscle advancement, hyoid myotomy, and bilateral maxillary advancement), and the like However, such surgeries, depending on types of surgery, need general anesthesia and a certain time of hospitalization after surgery and there is pain in a pharyngeal area for several weeks. Accordingly, there are many inconveniences such as eating soft food and the like.

Hence, recently, surgery to remove the entire uvula and a part of the palate using lasers has been developed. Here, laser surgery has an advantage of performing surgery only using local anesthesia and has disadvantages of repeatedly performing surgery several times at several week intervals and an increase in financial burden caused thereby.

In addition, the surgical treatment method has disadvantages in which a risk of relapse is present even when surgery is successful, postoperative complications such as pain, bleeding, infection, dysphagia, and the like may be caused, problems such as food coming out of the nose when eating, a voice change, and the like may be caused after surgery.

As the non-surgical treatment method for snoring, there is a method of forcing air into the respiratory tract by wearing an oxygen supply apparatus. Although the method has been reported as having a most outstanding effect, since expensive equipment is necessary and it is necessary to put a mask on the nose during sleep, discomfort is caused and carrying and handling are inconvenient.

In addition, recently, there has been developed a snoring prevention pillow configured to prevent snoring by supporting a rear part of the neck of a sleeper to allow the head to tilt backward when the sleeper lies back on the pillow so as to suppress the narrowing of the larynx and prevent snoring.

However, since a conventional snoring prevention pillow supports the back of the neck of a sleeper, the head tilts backward and thus is not stably supported such that a great load is applied to the back of the neck during sleep for a long time and the back of the neck is stiff and not refreshed.

Also, as the head tilts backward, a phenomenon that a mouth is opened during sleep occurs. When the mouth is opened during sleep, saliva preventing microbial growth in the mouth dries up such that microbial growth becomes active, thereby causing the occurrence of bad breath and periodontitis.

Also, when the mouth is opened during sleep, mouth breathing is performed instead of nose breathing. Generally, since oxygen saturation decreases in mouth breathing in comparison to nose breathing, lowered immunity is caused and thus a risk of disease development caused by a variety of germs or viruses increases.

Also, when a state in which the mouth is opened during sleep is maintained for a long time, the degree of tension of the temporomandibular joint and peripheral muscles thereof increases and thus temporomandibular joint dysfunction and facial asymmetry are caused.

DISCLOSURE

Technical Problem

The present invention is directed to providing a snoring prevention pillow configured to allow respiratory circulation to be smoothly maintained during sleep by inducing and supporting curved postures of the cervical spine and atlanto-occipital joint by allowing the head and neck of a sleeper to laterally rotate in any one of left and right directions and to extend in an upper lateral direction at the same time when the sleeper lies back on the pillow to sleep.

Technical Solution

One aspect of the present invention provides a snoring prevention pillow.

The snoring prevention pillow may include a central protruding portion (101) configured to allow the head and neck of a sleeper to laterally rotate from a vertical center of a pillow body (10) in any one of left and right directions.

The snoring prevention pillow may include a neck support portion (102) formed on a vertically lower side of the pillow body (10) in a lateral direction to allow the neck to extend.

The snoring prevention pillow may include a head rest portion (103) formed on each of both sides of the central protruding portion (101) and having a groove shape thinner than a thickness of the pillow body (10).

The head rest portion (103) may have a groove which deepens from the bottom to top in an upper lateral direction so as to allow the head and neck of the sleeper to extend in an upper lateral direction.

The central protruding portion (101) may be formed to protrude while a first inclined portion (101a) formed on each of both sides of the central protruding portion (101) may be connected to an inside of the head rest portion (103) having the groove shape.

The neck support portion (102) may be formed in a lateral direction while a second inclined portion (102b) may be formed on an upper portion thereof and connected to an inside of the head rest portion (103) having the groove shape.

The central protruding portion (101) and the neck support portion (102) may be formed to be connected to each other so as to induce the head to be seated on the head rest portion (103) and to allow the head and neck to laterally rotate and extend at the same time.

A center of the head rest portion (103) may be recessed to be inwardly inclined.

A hollow portion (103a) may be further provided in a center of the head rest portion (103) to pass therethrough in a vertical direction.

The inside of the pillow body (10) may be formed of a cushioning material having a cushioning force while a core (104) formed of a material firmer than the cushioning material may be formed in a central part of the cushioning material.

Advantageous Effects

According to the present invention, there is an effect of preventing snoring and sleep apnea in which when a sleeper lies back on a pillow to sleep, the head and neck of the sleeper rotate in any one of left and right directions and naturally extend due to a seating groove formed in an upper lateral direction at the same time so as to improve the maintenance of the respiratory tract by inducing a posture of turning the head aside from a supine position and extension and lateral rotation of the neck and to allow respiratory circulation to be smoothly maintained during sleep by inducing and supporting curved postures of the cervical spine and atlanto-occipital joint.

Also, since a rear side part of the head is stably supported, a load applied to the back of the neck can be reduced and thus a comfortable sleep position can be maintained so as to induce comfortable sleep.

Also, since the head and neck of the sleeper rotate in any one of left and right directions and thus the jaw is induced to be closed so as to suppress a mouth-opening phenomenon, a variety of diseases caused by the opening of the mouth during sleep can be prevented from occurring.

BEST MODE FOR INVENTION

Embodiments of the present invention will be described below in detail with reference to the attached drawings to be easily carried out by one of ordinary skill in the art. However, since the description on the present invention is merely a set of embodiments for a structural or functional description, the scope of the present invention should not be understood as limited to the embodiments disclosed herein. That is, since the embodiments may have a variety of changes and several forms, the scope of the present invention should be construed as including equivalents for implementing the technical concept thereof. Also, since this does not mean that purposes or effects of the present invention disclosed herein or only the effects should be included in a particular embodiment, it should be noted that the scope of the present invention should not be understood as limited thereto.

The meaning of the terms stated herein should be understood as follows.

The terms "first," "second," and the like are used for distinguishing one element from another, and thus the scope of the present invention is not limited to the terms. For example, a first component may be referred to as a second component, and the second component may also be referred to as the first component. When one component is referred to as being "connected to" another component, it should be understood that the one component may be directly connected to the other component or another component may be present therebetween. On the other hand, when one component is referred to as "directly connected to" another component, it should be understood that another component is not present therebetween. Meanwhile, other expressions describing a relationship between components, that is, "between" and "right between," "adjacent to" and "directly adjacent to," and the like should be equally construed.

Singular expressions, unless defined contextually otherwise, should be understood as including plural expressions. The terms "comprise," "have," and the like are intended to designate the presence of stated features, numbers, steps, operations, elements, component, or a combination thereof and should be understood as not precluding the possibility of the presence or addition of one or more other features, numbers, steps, operations, elements, components, or a combination thereof.

All the terms used herein, unless defined otherwise, have the same meanings as generally understood by one of ordinary skill in the art to which the present invention pertains. Terms defined in generally used dictionaries should be construed as having the meanings which coincide with contextual meanings in the related art and should not be construed as having ideal or excessively formal meanings unless clearly defined herein.

Figure 1:
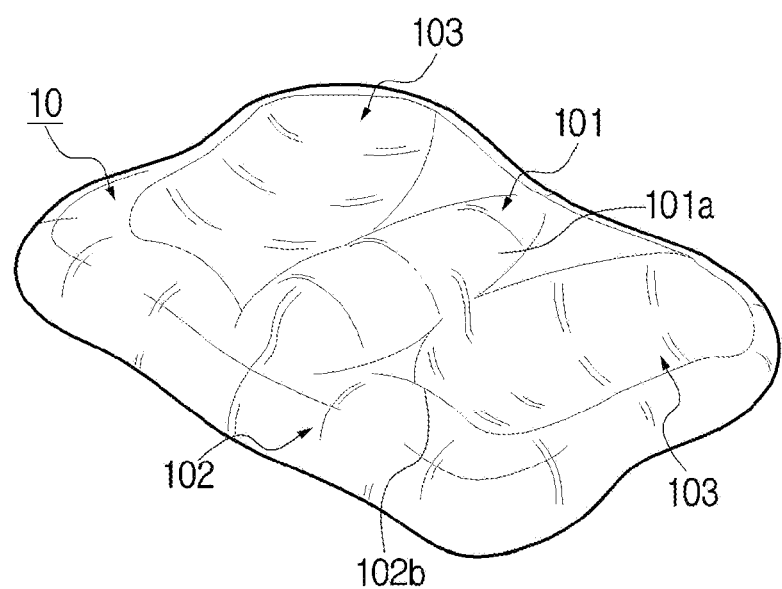
FIG. 1 is a perspective view illustrating one embodiment of a snoring prevention pillow according to the present invention.
Figure 2:
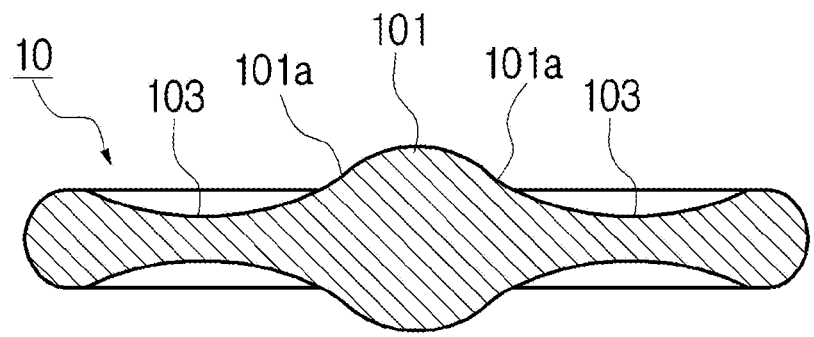
FIG. 2 is a cross-sectional view illustrating one embodiment of the snoring prevention pillow according to the present invention.
Figure 3:
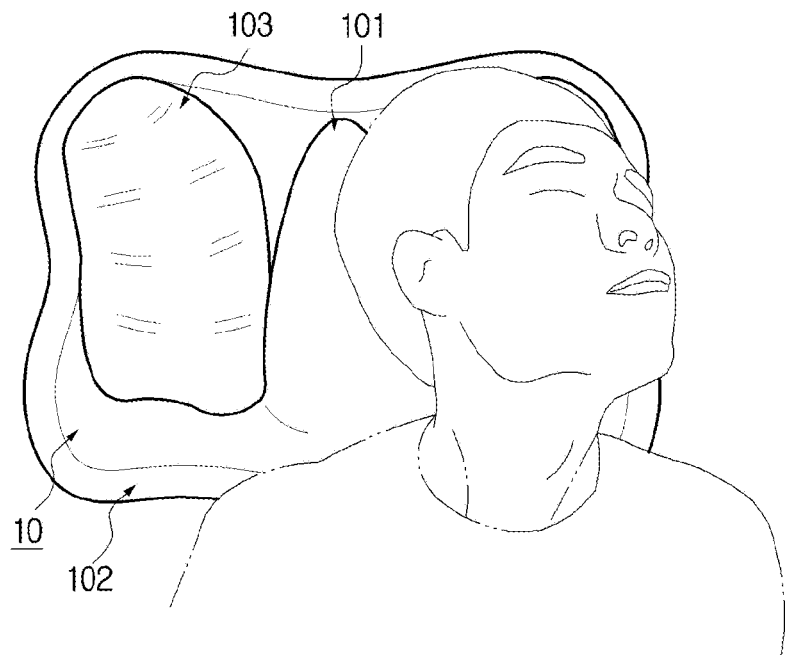
FIG. 3 is a view illustrating a usage state according to one embodiment of the snoring prevention pillow according to the present invention.

FIG. 1 is a perspective view illustrating one embodiment of a snoring prevention pillow according to the present invention, FIG. 2 is a cross-sectional view illustrating one embodiment of the snoring prevention pillow according to the present invention, and FIG. 3 is a view illustrating a usage state according to one embodiment of the snoring prevention pillow according to the present invention.

A description will be set forth with reference to FIGS. 1 to 3.

In the snoring prevention pillow according to the present invention, a pillow body 10 includes a central protruding portion 101, a neck support portion 102, and a head rest portion 103.

The pillow body 10 may be formed of an outer cover and a cushioning material filled in the outer cover or may be entirely formed of cushioning material.

When the pillow body 10 is formed of the outer cover and the cushioning material, a zipper fastener configured to fill or accommodate the cushioning material in the outer cover may be provided on one side of the outer cover.

Also, it should be noted in advance that a material of the outer cover may be a natural fabric having high air permeability but is not limited thereto.

It should be noted in advance that the central protruding portion 101 may be formed to protrude elliptically in a plane from a vertical center of the pillow body 10 so as to allow the head and neck of a sleeper to rotate in any one of left and right directions but is not limited thereto.

Here, a first inclined portion 101a formed on each of both sides of the central protruding portion 101 is formed to be connected to an inside of the head rest portion 103 formed to have a groove shape so that the head of the sleeper naturally performs lateral rotation to be seated in the head rest portion 103 when the sleeper lies back on the pillow body 10.

The neck support portion 102 may be formed lengthwise in a horizontal direction on a vertically lower side of the pillow body 10 and may have a thickness protruding thicker than a thickness between a flat surface and a bottom surface of the pillow body 10 so as to form an extension position of the neck.

Also, a second inclined portion 102b is formed on an upper side of the neck support portion 102 while formed to be connected to the inside of the head rest portion 103 having a groove shape.

Accordingly, when the neck is located on a part where the central protruding portion 101 and the neck support portion 102 meet, the lateral rotation and extension position of the neck occur at the same time and thus the head is naturally located on the head rest portion 103 to lie comfortably.

In addition, as the neck is supported by the neck support portion 102, the head of the sleeper is naturally seated on an inside of a concave groove of the head rest portion 103 so as to induce curved postures of the cervical spine and atlanto-occipital joint and thus the respiratory tract becomes wider and respiration is smoothly performed.

Also, an inwardly concave tensioning groove may be further provided on a lower side of the neck support portion 102.

The head rest portion 103 is formed on each of both sides of the central protruding portion 101 while having a groove thinner than the thickness of the pillow body 10.

Particularly, since the head rest portion 103 is formed to have a groove which deepens from the bottom to the top in an upper lateral direction, that is, in a direction toward a corner of the pillow body 10, when the head of the sleeper is seated on the head rest portion 103, the head and neck of the sleeper naturally extend in an upper lateral direction according to a shape of the head rest portion 103.

Accordingly, as a back side of the head of the sleeper which is seated on the head rest portion 103 to be surrounded by the inside of the head rest portion 103, the temporomandibular joint is brought into close contact with the inside of the head rest portion 103 and thus the mandible is pushed forward and the jaw is closed so as to prevent the mouth of the sleeper from opening during sleep and to improve respiration by widening the pharynx of the sleeper.

Also, since the back side of the head of the sleeper is stably supported by the inside of the head rest portion 103, a load of the head may be evenly distributed in the head rest portion 103 and thus a load applied to the cervical spine may be reduced so as to prevent neck or shoulder discomfort caused by sleeping for a long time.

Meanwhile, in a plan view, an angle of the head rest portion 103 may be formed to be 10 to 60° on the basis of a central line of the central protruding portion 101.

When the angle of the head rest portion 103 is smaller than 10°, the temporomandibular joint is not brought into close contact with the inside of the head rest portion 103 such that the mouth of the sleeper opens during sleep.

When the angle of the head rest portion 103 is greater than 60°, tension in neck or shoulder muscles is caused.

Figure 4:
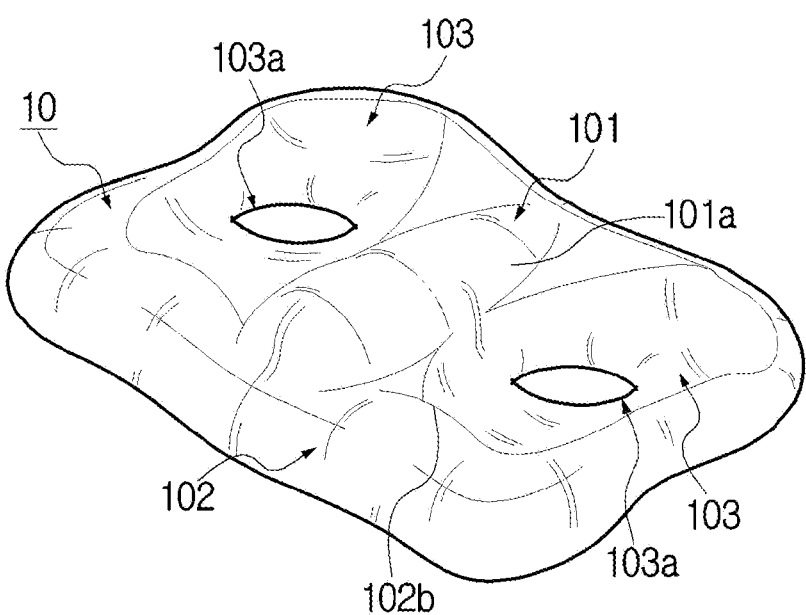
FIG. 4 is a perspective view illustrating a second embodiment of the snoring prevention pillow according to the present invention.

FIG. 4 is a perspective view illustrating a second embodiment of the snoring prevention pillow according to the present invention.

Referring to FIG. 4, a detailed description of components overlapping those of the above-described embodiment and components having the same reference numerals will be omitted.

A hollow portion 103a may be further provided in a center of the head rest portion 103 to pass therethrough in a vertical direction.

Accordingly, since the head of the sleeper is seated in the head rest portion 103 and thus the back side of the head of the sleeper is surrounded by the inside of the head rest portion 103, smooth ventilation may be secured to prevent sweating so as to sleep in a pleasant state.

Also, a pressure applied to an ear of the sleeper may be minimized by preventing an ear part of the sleeper which is seated in the head rest portion 103 from being brought into close contact with and pressed by the inside of the head rest portion 103 so as to provide a more stable sleeping posture.

Figure 5:
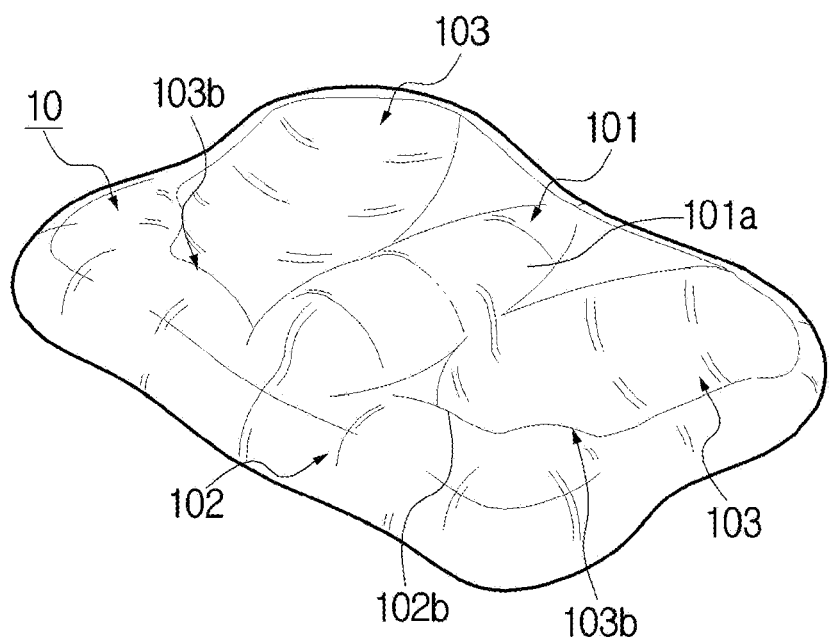
FIG. 5 is a perspective view illustrating a third embodiment of the snoring prevention pillow according to the present invention.

FIG. 5 is a perspective view illustrating a third embodiment of the snoring prevention pillow according to the present invention.

Referring to FIG. 5, a detailed description of components overlapping those of the above-described embodiments and components having the same reference numerals will be omitted.

A pressurizing protrusion portion 103*b* configured to pressurize the temporomandibular joint of the sleeper which is seated in the head rest portion 103 may be further provided on one side of the head rest portion 103.

Accordingly, when the head of the sleeper is seated in the head rest portion 103 and the back side of the head of the sleeper is surrounded by the inside of the head rest portion 103, the pressurizing protrusion portion 103*b* is more closely pressed against the temporomandibular joint and pushes the temporomandibular joint to close the jaw so as to more effectively prevent the mouth of the sleeper from being opened during sleep.

Figure 6:
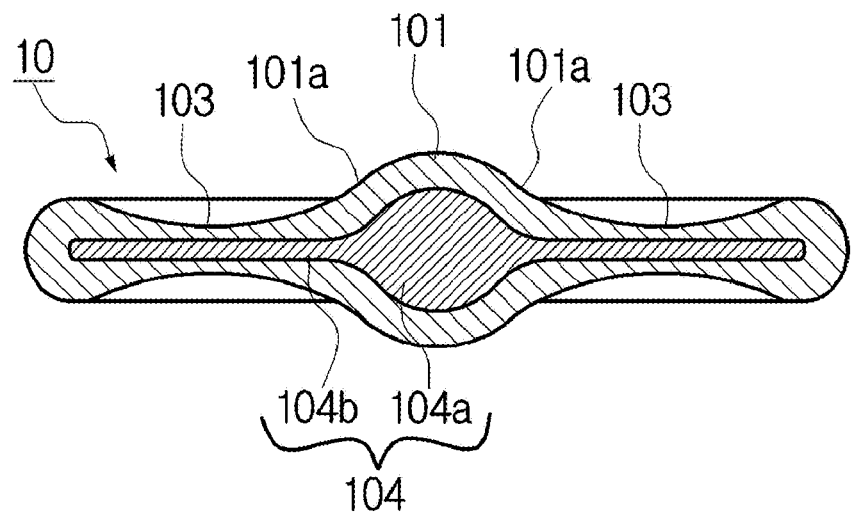
FIG. 6 is a cross-sectional view illustrating the third embodiment of the snoring prevention pillow according to the present invention.
Figure 7:
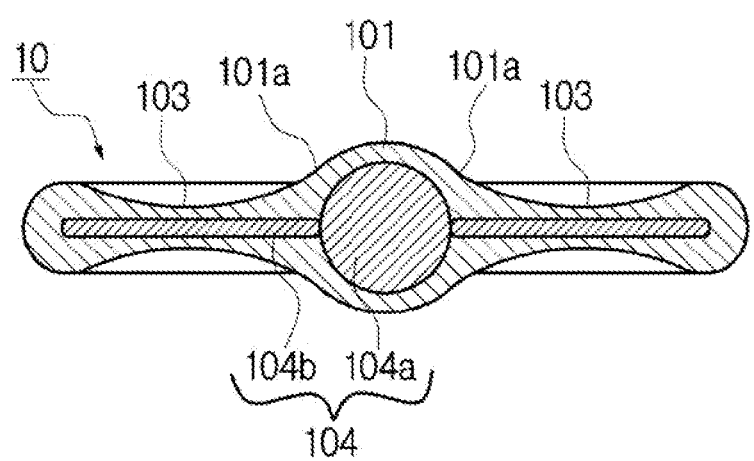
FIG. 7 is a cross-sectional view illustrating a fourth embodiment of the snoring prevention pillow according to the present invention.

FIG. 6 is a cross-sectional view illustrating the third embodiment of the snoring prevention pillow according to the present invention, and FIG. 7 is a cross-sectional view illustrating a fourth embodiment of the snoring prevention pillow according to the present invention.

Referring to FIGS. 6 and 7, a detailed description of components overlapping those of the above-described embodiments and components having the same reference numerals will be omitted.

The inside of the pillow body 10 is formed of a cushioning material having a cushioning force while a core 104 formed of a material firmer than the cushioning material may be formed in a central part of the cushioning material.

The core 104 includes a first core 104*a* and a second core 104*b*.

Since the first core 104*a* has a cylindrical shape and is formed in the central protruding portion 101 in a longitudinal direction, when the sleeper lies back on the pillow body, an excessive depression of the central protruding portion 101 is suppressed and structural strength thereof is maintained so as to allow the neck and head of the sleeper to smoothly rotate in any one of left and right directions.

Since the second core 104*b* has a plate shape having a certain thickness on each of both sides of the first core 104*a* and is formed in the head rest portion 103, when the sleeper lies back on the pillow body, an excessive depression of the head rest portion 103 is suppressed and structural strength thereof is maintained so as to stably support the head of the sleeper. Accordingly, as a weight of the head is evenly distributed in the head rest portion 103, a load applied to the cervical spine may be reduced and thus a curved posture of the atlanto-occipital joint may be uniformly maintained so as to prevent neck or shoulder discomfort caused by sleeping for a long time.

As a material of the core 104, materials such as sponge, memory foam, latex, and the like, which maintain a certain shape without an external physical stimulus and have a high cushioning feeling and elasticity so as to absorb and relax an external physical stimulus and to be restored to an original shape when the physical stimulus is relieved, may be used.

Also, it should be noted in advance that the first core 104*a* and the second core 104*b* may be integrally formed or separately formed and have different materials and different strengths when they are separately formed.

The above embodiments of the present invention are not implemented only using the above-described apparatus and/or operating method and may be implemented using a program configured to implement a function corresponding to the components of the embodiments of the present invention, a recording medium on which the program is recorded, and the like which are easily implementable by an expert in the art to which the present invention pertains from the above description.

Also, although the embodiments of the present invention have been described above in detail, the scope of the present invention is not limited thereto and a variety of changes and modifications made by those skilled in the art using the basic concept of the present invention defined by the following claims also belong to the scope of the present invention.

The invention claimed is:

1. A snoring prevention pillow comprising:
   central protruding portions (101) formed to protrude from central portions of an upper surface and a lower surface of a pillow body (10) and configured to laterally rotate a head and a neck of a sleeper in any one of left and right directions;
   a neck support portion (102) formed under the pillow body (10) in a lateral direction to allow the neck to extend; and
   head rest portions (103) each formed at one of both sides of the central protruding portion (101) and having a groove shape that is thinner than a thickness of the pillow body (10),
   wherein first inclined portions (101*a*) at both sides of the central protruding portion (101) are each formed to continue from an inner surface of the head rest portion (103) formed in the groove shape,
   a second inclined portion (102*b*) is formed on an upper portion of the neck support portion (102) and formed to continue from the inner surface of the head rest portion (103) formed in the groove shape,
   the central protruding portion (101) and the neck support portion (102) are formed to be connected to each other so as to guide the head to be seated on the head rest portion (103),
   a central portion of the head rest portion (103) is formed to have an inward inclination grade,
   an inside of the pillow body (10) is filled with a cushioning material having a cushioning force, and
   a core (104) made of a material that is firmer than the cushioning material is formed in a central portion of the cushioning material,
   wherein the core (104) includes a first core (104*a*), which has a cylindrical shape and is vertically formed inside the central protruding portion (101) to prevent an excessive recess of the central protruding portion (101) and maintain structural strength of the central protruding portion (101) so that the head and the neck of the sleeper smoothly rotate in any one of the left and right directions, and
   second cores (104*b*) which are each formed in a plate shape with a predetermined thickness at one of both sides of the first core (104*a*) inside the head rest portion (103) to prevent an excessive recess of the head rest portion (103) and maintain structural strength of the head rest portion (103) so that the head of the sleeper is stably supported and a weight of the head is evenly distributed inside the head rest portion (103).

\* \* \* \* \*